(12) United States Patent
Shaw et al.

(10) Patent No.: US 7,187,437 B2
(45) Date of Patent: Mar. 6, 2007

(54) PLURALITY OF LIGHT SOURCES FOR INSPECTION APPARATUS AND METHOD

(75) Inventors: Eugene L. Shaw, Lake Orion, MI (US); Forrest S. Wright, Rochester, MI (US)

(73) Assignee: Shearographics, LLC, Lake Orion, MI (US)

( * ) Notice: Subject to any disclaimer, the term of this patent is extended or adjusted under 35 U.S.C. 154(b) by 113 days.

(21) Appl. No.: 11/067,256

(22) Filed: Feb. 25, 2005

(65) Prior Publication Data

US 2005/0200838 A1 Sep. 15, 2005

Related U.S. Application Data

(63) Continuation-in-part of application No. 10/659,466, filed on Sep. 10, 2003, now Pat. No. 6,934,018.

(51) Int. Cl.
G01B 9/02 (2006.01)
G01N 21/00 (2006.01)

(52) U.S. Cl. ..................... 356/237.2; 356/520
(58) Field of Classification Search ............ None
See application file for complete search history.

(56) References Cited

U.S. PATENT DOCUMENTS

| 4,506,981 A | 3/1985 | Hoff, Jr. |
| 4,887,899 A | 12/1989 | Hung |
| 5,065,331 A | 11/1991 | Vachon et al. |
| 5,473,434 A | 12/1995 | de Groot |
| 5,481,356 A | 1/1996 | Pouet et al. |
| 5,671,050 A | 9/1997 | de Groot |
| 5,760,888 A | 6/1998 | Rottenkolber |

(Continued)

FOREIGN PATENT DOCUMENTS

EP 1043578 A2 10/2000

OTHER PUBLICATIONS

International Search Report dated Jul. 18, 2006 of PCT/US06/06254.

(Continued)

*Primary Examiner*—Michael P. Stafira
(74) *Attorney, Agent, or Firm*—William J. Schramm

(57) ABSTRACT

Described is an anomaly detector apparatus 10 for detecting an anomaly in a substrate, e.g., a tire comprising: a source of coherent light 20 to shine the light 27 directly onto the tire surface 24 and the light being reflected 32 from the tire; a stressing apparatus 12, which is juxtaposed to the tire and which, can optionally stress the tire; a reflected light receiving apparatus 40 for receiving the light 32 reflected directly from the tire surface 24 whether the tire is in a stressed or unstressed condition; a comparator 44 which views and compares images of reflected light from the reflected light receiving apparatus 40 when the tire is stressed or unstressed thereby ascertaining an anomaly in the tire and generates an output from the comparison; and a display apparatus 46 electronically connected to the comparator for displaying the output from the comparator. Also described is a plurality of sources 100 and light receiving apparatus 102 sitting atop a vertically moving support structure 110 that may view 360 degrees, of the whole circumferential interior surface of the tire.

26 Claims, 11 Drawing Sheets

U.S. PATENT DOCUMENTS

| | | |
|---|---|---|
| 5,826,319 A | 10/1998 | Colwell et al. |
| 6,006,599 A | 12/1999 | Kelm-Klager et al. |
| 6,012,329 A | 1/2000 | Kelm-Klager et al. |
| 6,041,649 A | 3/2000 | Fembock |
| 6,188,482 B1 | 2/2001 | Cloud |
| 6,188,483 B1 | 2/2001 | Ettemeyer |
| 6,268,923 B1 | 7/2001 | Michniewicz et al. |
| 6,285,447 B1 | 9/2001 | Parket et al. |
| 6,362,873 B1 | 3/2002 | Facchini et al. |
| 6,433,874 B2 | 8/2002 | Lindsay et al. |
| 6,493,092 B1 | 12/2002 | Marklund |
| 6,496,254 B2 | 12/2002 | Bostrom et al. |
| 6,522,410 B1 | 2/2003 | Marcus et al. |
| 6,542,249 B1 | 4/2003 | Kofman et al. |
| 6,556,290 B2 | 4/2003 | Maeda et al. |
| 6,584,215 B1 | 6/2003 | Mahner |
| 6,791,695 B2 | 9/2004 | Lindsay et al. |
| 6,840,097 B1 | 1/2005 | Huber et al. |
| 6,876,458 B2 | 4/2005 | Kraus |
| 2002/0135751 A1 | 9/2002 | Steinbichler |
| 2004/0212795 A1 | 10/2004 | Steinbichler |

OTHER PUBLICATIONS

Y, Y, Hung, etal Full-field Optical Strain Measurement having Postrecording Sensitivity and Direction Selectivity, Presented at 1975 SESA Spring Meeting, Chicago, IL May 11-16.

Wolfgang Steinchen and Lianxiang Yang, Digital Shearography Theory and Application of Digital Speckle Pattern Shearing Interferometry, 2003, pp. 30-35, SPIE Press.

AST 4000 Series Shearography Tire Inspection Systems, Laser Technology Inc. of Norristown, PA dated Sep. 1996.

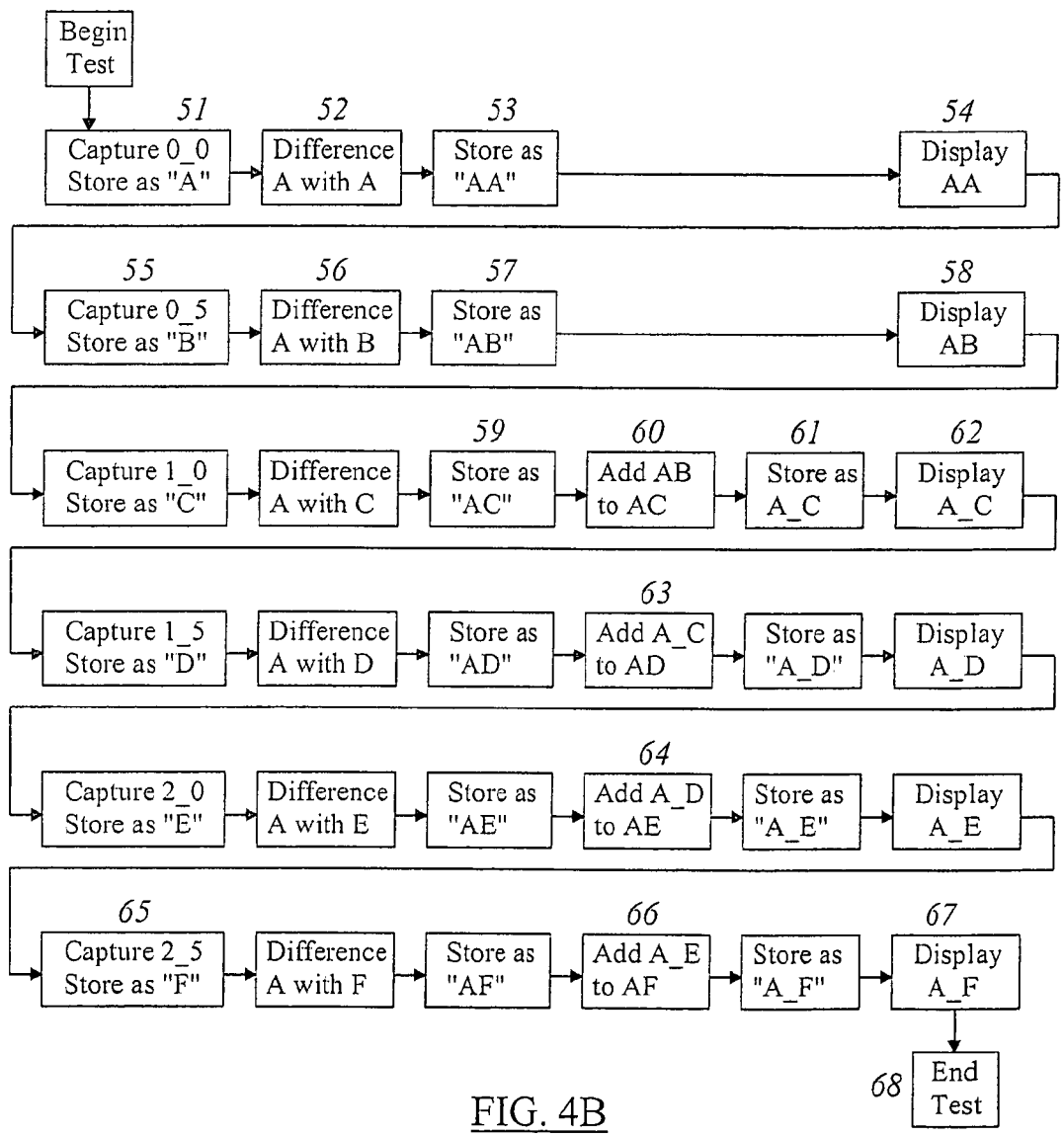

US 7,187,437 B2

PLURALITY OF LIGHT SOURCES FOR INSPECTION APPARATUS AND METHOD

CROSS-REFERENCE TO RELATED APPLICATION

This application is a continuation-in-part of U.S. patent application Ser. No. 10/659,466, filed Sep. 10, 2003, now U.S. Pat. No. 6,934,018 hereby incorporated by reference.

FIELD OF THE INVENTION

The present invention pertains to the field of Non-Destructive Testing (NDT) of a variety of substrates and the ability to illuminate and capture reflected light efficiently from those substrates. In particular the invention pertains to such testing of tires, utilizing a computer for automated output display of an image of the tested tire.

BACKGROUND OF THE INVENTION

For many years the standard practice for calibrating shearographic/holographic tire testing machines has been ASTM F1364-92. This test method describes the construction and use of a calibration device for demonstrating the anomaly detection capability of an interferometric laser imaging non-destructive tire inspection system. A typical shearographic fringe pattern resulting from such testing technique is shown in FIG. 1.

As has been described in U.S. Pat. No. 6,433,874 the technique of shearing interferometry, or shearography involves the interference of two laterally-displaced images of the same object to form an interference image. Conventional shearographic methods require that a first interference image (or baseline image) be taken while the object is in an unstressed or first stressed condition, and another interference image be taken while the object is in a second stressed condition. Comparison of those two interference images (preferably by methods of image subtraction) reveals information about the strain concentrations and hence the integrity of the object in a single image called a shearogram. FIG. 1 shows an image which is the direct result of two laterally-displaced images being obtained by an interference technique. The images that are obtained are not to the scale of the anomaly in the tire. In addition very minute anomalies, those in the order of 1.7 mm are not readily ascertainable from a shearogram such as that shown in FIG. 1.

While some systems for shearography have an output such as the display of computerized systems of the '874 patent, many of the systems utilized are such that they have an output of highly sensitive film which is extremely costly and requires a special viewing device. Further, film based shearographic tire testing machines (and individual tire tests) are typically very expensive therefore a limited number are utilized in the industry within individual plants.

The electronic shearography of the '874 patent is based upon the shearography described in U.S. Pat. No. 4,887,899 which describes an apparatus which produces an interference image by passing light, reflected from the test object, through birefringent material and a polarizer. The birefringent material splits a light ray into two rays and polarizing it makes it possible for light rays reflected from a pair of points to interfere with each other. Thus each point on the object generates two rays and the result is an interference image formed by the optical interference of two laterally displaced images of the same object.

There is a need for improved tire testing technique and apparatus which facilitate direct measurements which permit a quantitative analysis or a scalability of the anomaly in the tire.

There is a need to obtain an output from tire testing equipment which does not rely upon an interferogram or proprietary optics, thereby making the output of such testing technique accurately describe and identify the anomaly.

There is a need for a tire testing technique and apparatus which permits the utilization of coherent light and the reflection of such light to be captured by inexpensive equipment and displayed using commonly available computerized systems.

It is accordingly an object of the invention to provide an approved tire testing technique and apparatus which facilitates direct measurements, and a quantitative analysis or scalability of the anomaly in the tire.

It is an object of the present invention to provide a tire testing technique and apparatus which does not rely upon an interferogram to accurately describe and identify the anomaly.

It is an object of the present invention to provide a tire testing technique and apparatus which permits the utilization of coherent light and reflection of such light to be captured by inexpensive equipment and displayed using commonly available computerized systems which does not utilize laterally-displaced images but a single image of the anomaly as output.

SUMMARY OF THE INVENTION

Described is an anomaly detector apparatus for detecting an anomaly in a substrate comprising a plurality of sources of coherent light to shine the light directly onto the substrate surface and the light being reflected from the substrate; a stressing apparatus, which is juxtaposed to the substrate and which, can optionally stress the substrate; a plurality of reflected light receiving apparatus for receiving the light reflected directly from the substrate whether the substrate is in a stressed or unstressed condition, wherein the sources of light are spaced to shine simultaneously on the entirety of the substrate surface to be tested and all of the receiving apparatus are spaced to receive the reflected light simultaneously to detect an anomaly on all substrate surfaces on which the light is shown a comparator which views and compares images of reflected light from the reflected light receiving apparatus when the substrate is stressed or unstressed thereby ascertaining an anomaly in the substrate and which generates an output from the comparison; and a display apparatus electronically connected to the comparator for displaying the output from the comparator.

Also described is a method of detecting an anomaly in a substrate comprising providing a plurality of sources of coherent light; shining the light directly onto the substrate surface, thereby generating a reflected light from the substrate; stressing the substrate; providing a plurality of reflected light receiving apparatus for receiving the light reflected directly from the substrate whether the substrate is in a stressed or unstressed condition, wherein the sources of light are spaced to shine substantially simultaneously on the entirety of the substrate surface to be tested and all of the receiving apparatus are spaced to receive the reflected light substantially simultaneously to detect an anomaly on all substrate surfaces on which the light is shown; providing a comparator which views and compares images of reflected light from the reflected light receiving apparatus when the substrate is stressed or unstressed thereby ascertaining an anomaly in the substrate and generates an output from the comparison; and displaying, from apparatus electronically connected to the comparator, the output from the comparator.

BRIEF DESCRIPTION OF THE DRAWINGS

These and other objects, features and advantages of this invention will be apparent from the following detailed description, appended claims and accompanied drawings in which;

FIG. 4A is a legend for FIG. 4B. This legend serves to name the images captured with the tire subjected to various levels during the sequence of steps used in FIG. 4B;

FIG. 4B is a block diagram of the sequences of computations of a computer to capture and process different images of the unstressed and stressed conditions as the typical stressing conditions are applied, such as an application of vacuum;

DETAILED DESCRIPTION OF THE INVENTION

Definitions

Figure 1:
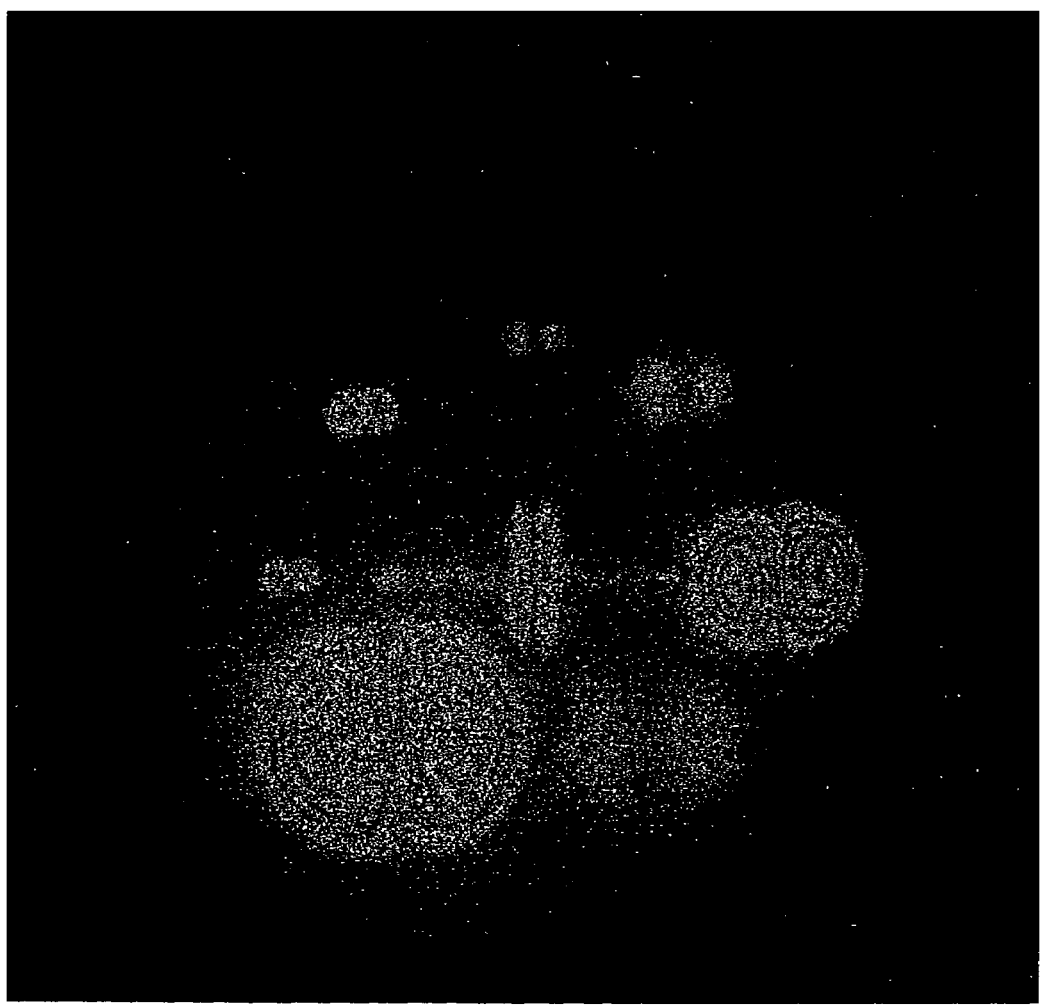
FIG. 1 is a prior art shearogram obtained from a testing fixture identified in ASTM 1364-92.

Anomaly is defined as a defect in a tire which can generally be characterized as air trapped in a cured tire as a result of variations in the thickness of the tire components; porosity and voids in the tire, a separation, an undercure of the tire, trapped air and bubbles; low interply adhesion, poor cord adhesion, bare wires, broken cords, and machine building errors.

Bitmap is a data file or structure which corresponds bit for bit with an image displayed on a screen, preferably in the same format as it would be stored in the display's video memory or alternatively as a device independent bitmap. A bitmap is characterized by the width and height of the image in pixels and the number of bits per pixel which determines the number of shades of grey or colors it can represent.

Coherent light is a light having a single wavelength, frequency and phase. It is also radiant electromagnetic energy of the same, or almost the same wavelength, and with definite phase relationships between different points in the field.

Differenced or also known as delta frame means an animation frame that contains only the pixels different from the preceding key frame.

Diffuser is an apparatus which transmits light through a translucent material which permits the distribution of incident light onto the tire to be tested.

Interferometer is an instrument in which light from a source is split into two or more beams which are subsequently reunited after traveling over different paths and display interferences.

Laser is a device that produces a beam of coherent or monochromatic light as a result of photon-stimulated emission. Such beams have a single wavelength and frequency. Materials capable of producing this effect are certain high period crystals such as ruby, yttrium garnet, metallic tungstates or molybdates doped with rare earth ions; semiconductors such as gallium arsenide, neodymium-doped glass; various gasses, including carbon dioxide, helium, argon, neon, and plasmas, and the like.

Laterally-displaced is a term that means, what appears to be a double or side by side image but is actually a positive and negative optical interference of a single anomaly. Further laterally means side by side but depending on the orientation of the optical element in the device could be any angle.

In this form of Non-Destructive Testing (NDT), non-destructive means a testing technique where the object to be tested is subjected to a stressing element and at the end of the testing the object is reverted to substantially its original condition.

The processor is a device or software, usually a central processing unit; it can also be a program that transforms some input into some output such as a computer or linkage editor; it facilitates the comparisons of images; it may be a hardwired device using embedded instructions to perform the comparisons.

Stressing element means an element that is used to apply stress or strain to an object to cause a change from its original condition. Such stressing can take the form of the application of a vacuum, the application of light, the application of a gas, the application of a mechanical force to permit flexing, the application of acoustical sound thereby vibrating the tire, or some other vibrating technique or application of heat and the like.

Reference is made to co-pending patent application U.S. Ser. No. 11/066,672 filed Feb. 25, 2005 entitled Non-Destructive Testing and Imaging, hereby incorporated by reference.

In general, the apparatus and method of the present invention can be described as follows:

The inside surface of the tire is a diffuse reflective surface, verses a mirror which is a specular reflective surface. A speckle pattern is visible on diffuse rather than specular reflective surfaces that is illuminated with laser light. These reflections from the anomalous regions change during the stressing cycle as the surface deforms. With multiple images captured by the camera during this cycle, the computer can process the image information using a software algorithm such as that described in FIG. 4A and FIG. 4B. In the present invention light does not pass through a birefringent material or a shearing optic material.

A typical test setup for the present invention is described as follows: The tire to be inspected is placed horizontally on a plate within a vacuum chamber. A commonly available industrial digital camera sits in the center of the tire so as to view a region of the inside surface of the tire such as camera model LU-205C available from Lumenera Corporation of Ottawa, Ontario, Canada (Lumenera.com) which is a color 2.0 megapixel having SVGA (800×600) sub-sampling which provides 40 frames/sec. The digital camera uses a commonly available lens to set the focus of the reflected speckle pattern image of the tire region on the digital image sensor. Preferably, the lens is adjusted so that the image is out of focus. The lens is preferably turned as far as possible towards a "near" setting of the lens (e.g. counter-clockwise when looking at the camera and lens).

A cable connects the camera to a computer. Image information is sent through this cable to the computer memory. Images from memory can be viewed on the computer display in near real-time, i.e., as the images are captured and processed by the equipment.

Generally each image will be stored in memory as a black/white bitmap file whereby 8 bits are used to store the gray-scale levels of each image sensor picture element, or pixel, value. Likewise, the images viewed on the computer display will be of the form of 8-bit, gray-scale, bitmap display images corresponding to the bitmap images, as the images are stored in memory. There are $2^8=256$ (from 0 to 255 decimal) possible gray-scale 8-bit values associated with each pixel of the displayed images. The decimal value, "0," as it directly represents the gray-scale level of individual display image pixels, corresponds to a black pixel, the darkest gray-scale pixel. Similarly, the decimal value, "255," represents the lightest gray-scale pixel, which is "white." The remaining numeric values between 0 and 255 represent a progression of gray levels from dark to light.

Note that two digital images that are exactly equivalent will have the same numeric values, from 0 to 255, for every image pixel.

Conversely, two digital images that are not equivalent will not have the same numeric values for every image pixel. The arithmetic difference between every corresponding image pixel of two exactly equivalent digital images will be 0. This means that the difference image obtained from differencing two equivalent digital images will be displayed as a totally black image. The difference image obtained from differencing two dissimilar digital images will not be a totally black image. The image differencing function provides a tool for observing slight changes between two digital images.

In one embodiment the stressing element is the use of vacuum. The speckle pattern associated with a given region of a tire will change with very small deformations of the tire surface. Such surface deformation occurs when the pressure drops in the vacuum test chamber and the air inside of a ply separation expands creating a deformation on the interior tire surface.

Practically speaking the two speckle pattern images of a tire surface region where there exists an underlying localized ply separation will be different if the two images are taken at different vacuum levels. Also the images will only, or at least ideally, be numerically different in the deformation region associated with the ply separation. The difference image of the two images will be black everywhere except the area where the deformation occurs. In the deformation region of the image there will be grey pixels of various shades. The deformation region is visible in the differenced image.

In one embodiment of the test method, six digital images of a laser illuminated interior surface region of a tire are taken with each image taken at one-of-six vacuum levels. The laser is a gallium arsenide laser having a wavelength of 808 nm (nanometer), model UH5-200 808 supplied by World Star Tech. of Toronto, Ontario, Canada (worldstartech.com). The first image will be taken at 0.0" Hg (atmospheric pressure). This first image will be called the base image. The five remaining images will be taken respectively at 0.5, 1.0, 1.5, 2.0, and finally 2.5" Hg. The six images will be stored in computer memory. Next five differenced images will be obtained using the base image always as one of the two images to be differenced. The other images used to make the five differenced images will be the five non-base images. Each of the five differenced images will be processed to filter out noise and increase contrast/brightness. Other processing may also be used. Any combination of available or custom image processing software including: auto anomaly detection, special effects, filtering, noise reduction, sharpening, dilation, colorization, positive or negative or the like. The five processed images will be added together in an accumulative fashion. After each addition of two images, the new image formed by the addition will be processed. The final image will be used for evaluation for the given tire region. There will be a plurality of inspection regions inspected using the preferred test method in order to evaluate the complete tire.

It is to be appreciated that a display is meant to cover varied electronic output of the images whether visible to the naked eye or not and includes a screen display, hard copy or an electronic image. The electronic image may be used by a computer to determine whether the test object passes or fails testing criteria without actually displaying the image to the naked eye and optionally without operator intervention.

Turning now to the drawings in the case.

FIG. 1 is a prior art shearogram obtained from the testing fixture identified in ASTM F 1364-92. For ease of readability, FIG. 1 is a black on white image as opposed to a white on black image which is one output from the ASTM test. It should be noted that the anomalies in that output are laterally-displaced images.

Figure 2:
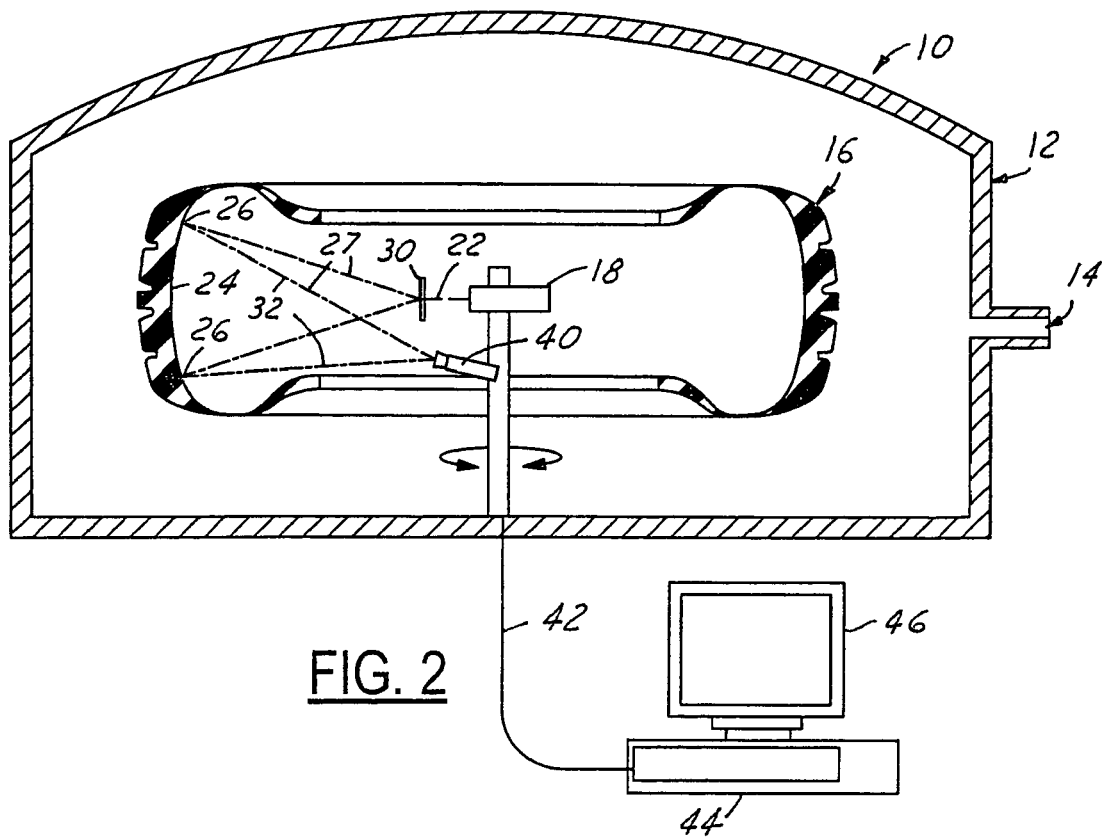
FIG. 2 is a schematic representation of the apparatus of the present invention.

FIG. 2 is a schematic diagram of the anomaly detector apparatus of the present invention. In general, the anomaly detector apparatus 10 is encased within a vacuum chamber 12 which is indicated as having a vacuum outlet 14. The tire 16 can be placed on a carrying member (not shown) and can be placed on a motorized conveyer (not shown) outside the vacuum chamber and moved into the vacuum chamber. Such techniques are well known in the art. The anomaly detector apparatus is comprised of the laser 18 mounted on a shaft 20 which can be rotated as well as moved forwards and back in the vacuum apparatus. The coherent light 22 emitted from the laser 18 reflects on the inner surface 24 of the tire at points 26 as well as numerous other points. The coherent light 22 from the laser 18 is passed through a diffuser 30 which facilitates the spreading of the light across the portions of the tire substrate 24 to be viewed. The diffused light 27 is reflected off of the points 26 in a speckled fashion which are reflected off of the substrate 24 as shown by beams 32. The light is speckled and is captured in a camera 40. Preferably, the camera or cameras are a CCD variety well known in the industry as a charged coupled device. Other photosensitive detection equipment may be utilized. The camera can be called an image sensor, namely, it senses the speckled image 32 from the application of direct laser light onto the tire surface 24.

The diffuser is a holographic diffuser of 25 mm diameter with relatively high diffuser transmission efficiency. Alternatively the diffuser may be opal diffusing glass having a diameter of 25 millimeter, both available from Edmund Industrial Optics of Barrington, N.J.

The camera and the computer are electrically connected through wire 42. It is to be appreciated that while electrical current may be necessary for the operation of the laser and the camera, the output from the camera could likewise be supplied to the computer 44 by well known wireless communication techniques represented by parallel lines 43. The computer hard drive 44 with a video card is attached to a monitor 46 for display of the speckled output 32.

Figure 3A:
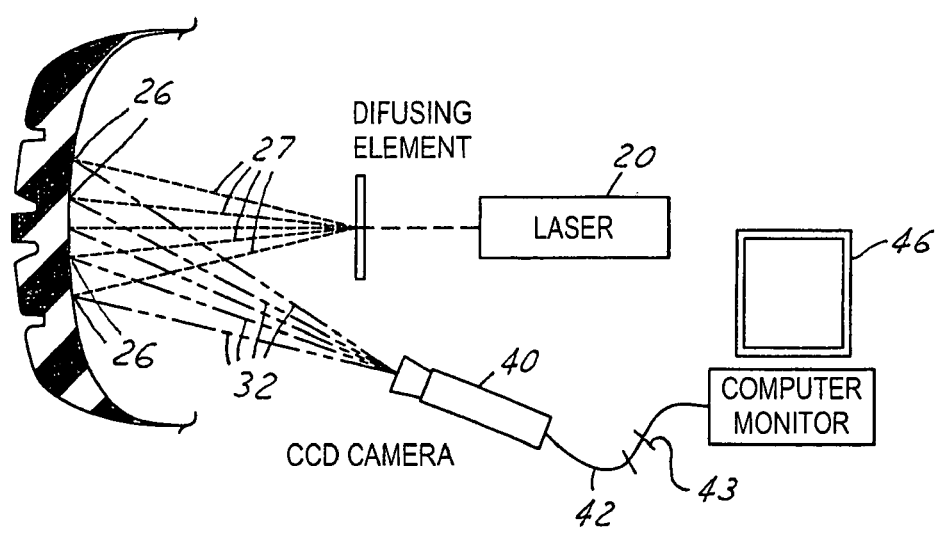
FIG. 3A is a schematic drawing of the tire testing equipment where the tire is in an unstressed condition.
Figure 3B:
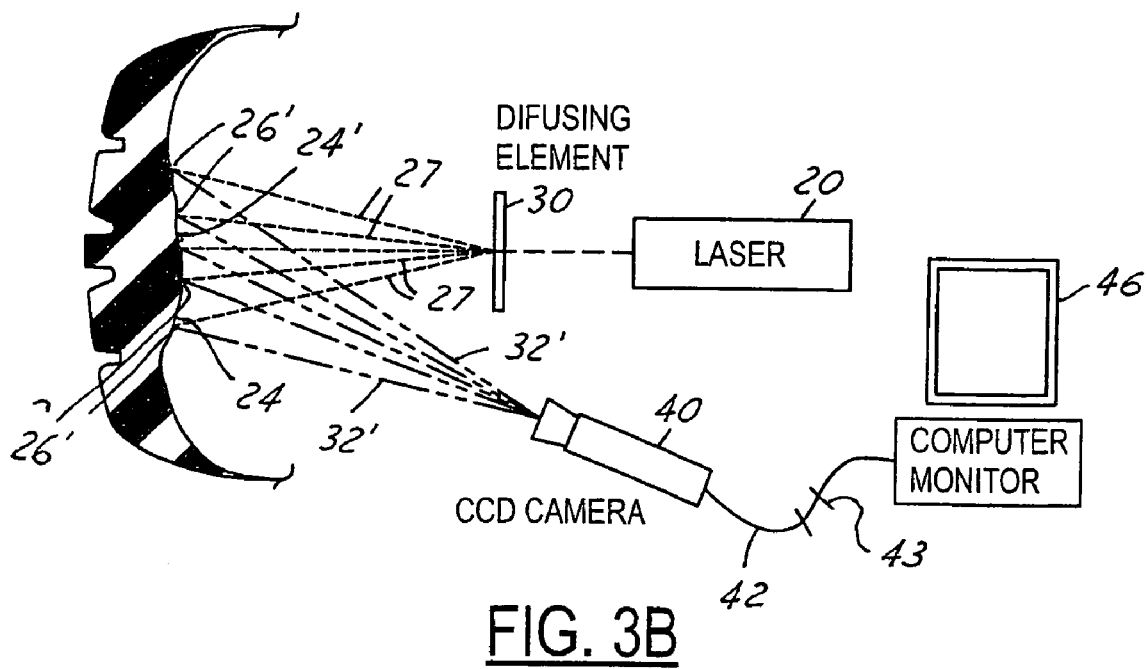
FIG. 3B is a schematic drawing of the tire testing equipment where the tire is in a stressed condition.

It is to be appreciated that the coherent laser light that is diffused onto the substrate 24 is reflected off of the substrate and the capturing is a direct capture of the reflections 32 by the CCD 40. This is unlike that which is utilized in prior art shearograms or interferometry which use an optical shearing device. The direct output of the device shown in FIGS. 2, 3A and 3B is that shown in FIG. 5. It is to be appreciated that the output of FIG. 5 can be either black on white or white on black depending on how one wishes to view the desired output. Because the image is captured by an image sensor, each pixel of the image can be identified or stored in digital form, as such, one can assign colors to different portions of the image, besides a white or black color thereby enhancing the image.

In a similar fashion, the operation of the equipment is shown in FIGS. 3A and 3B where there are larger number of diffused rays 27 at different points 26. The light 27 from the diffusing element 30 is dispersed as is shown in FIGS. 2, 3A and 3B.

After the tire is subjected to a stressing element such as application of a vacuum, the application of light, the application of gas, the application of a mechanical force to permit flexing, the application of acoustical sound thereby vibrating the tire or some other vibrating technique or heat application, the result is the movement of the tire substrate 24 which in turn causes a reflection of the laser light from points 26. FIG. 3B shows in an exaggerated fashion the variation from the smooth surface 24 of the tire to an expanded version or deformation 24 that is depicted. The laser light therefore is deflected at a different angle and therefore is shown as reflected speckled light 32 which creates images that are captured by the CCD camera 40.

The electrical cable 42 is shown as having parallel marks 43 to indicate that there may not necessarily be a direct wire for passing the images from the camera to the computer monitor but may be done by a wireless technique. The capturing of images on a camera is well known in the art. It can take the form of animation of images, which techniques are well known.

Figure 5:
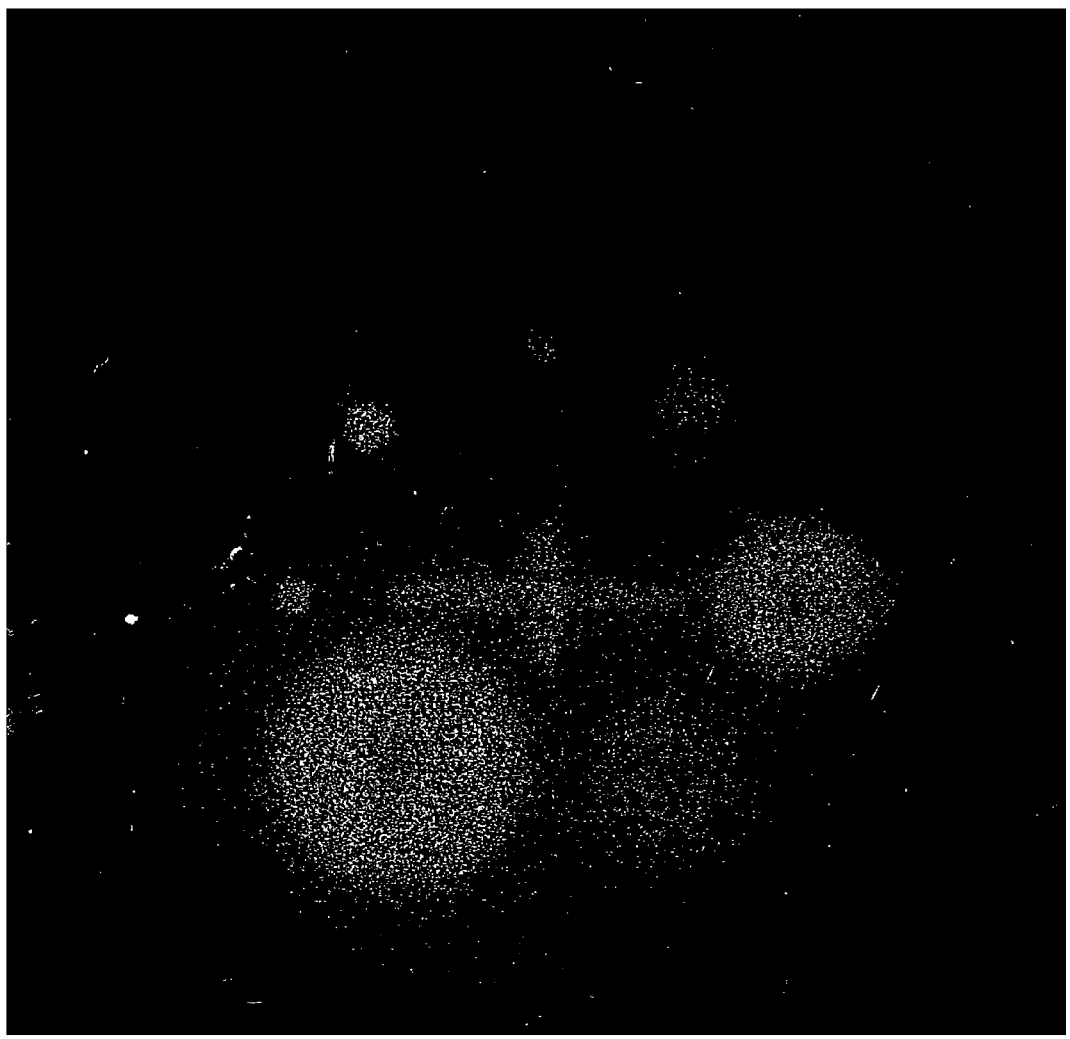
FIG. 5 is a typical output of the tire testing apparatus showing a calibration block used as the test object, and method of the present invention.

To graphically explain how the animation occurs reference can be made to FIGS. 4A and 4B. FIG. 4A shows a legend whereby images that are captured at various vacuum levels are given names for reference purposes. FIG. 4B shows the sequence of steps used for evaluating one region of the inside surface of a tire. The test sequence begins at the box designated as 50 and ends at step 68. At 51 the base image of the tire region is captured while the tire is unstressed and subjected to 0.0" Hg (atmospheric pressure). From the legend shown in FIG. 4A, this image is designated 0_0. This base image, referenced as 0_0, is stored as image "A" during step 51. For consistency, at box 52, the base image is differenced with itself to provide a black image that is displayed as the first image of the animation. This image is stored at 53 as "AA". It can be appreciated that a black image could have been produced in software without actually imaging the tire region, however, the base image "A" is captured since it is used in subsequent steps of the test sequence. After image AA is displayed at 54 the next image is captured at step 55 while the tire is subjected to 0.5" Hg vacuum. This image, "_5," is stored as "B" in step 55. At 56 the image, B, is differenced with the base image, A, producing image, "AB," which is stored in step 57. AB is then displayed at 58 and AB serves as the $2^{nd}$ image in the animation sequence. At step 60, as well as subsequent steps, 63, 64, 66, the previously displayed image is added to the image formed in the immediately preceding steps. For example, at step 60, the previously displayed image is AB and the image added to this image is the just-formed image, "AC" stored at step 59. The newly formed image is stored as "A_C" at step 61. A_C is then displayed at step 62. During the course of the test, images are captured at 0.5" Hg increments with the final image, "2_5," being captured with the tire subjected to 2.5" Hg vacuum (step 65). At 67 the final image in the animation sequence is displayed. The Images obtained during the tire test can be the subject of a printed output as shown in FIG. 5. A representative of such a technique is shown at FIG. 5 where the procedure, as followed in the ASTM testing technique described above, was utilized, except the apparatus of FIGS. 1 and 2 were used in place of an interferometer technique.

It is also to be understood that even though FIGS. 4A and 4B, show the vacuum cycle from 0.0 Hg. to 2.5 Hg, any combination of vacuum levels or set points increasing or decreasing may be used. As an example from 5.5 Hg. to 1.0 Hg.

In another embodiment of the invention, an assembly 104 including a plurality of reflected light receiving apparatus for receiving the light reflected is utilized such as that shown in FIGS. 6–8A. In this embodiment, the anomaly detector apparatus 10 is modified by redesigning the assembly of the source of coherent light 18 to better facilitate the light distribution on the inside of the outside of a hollow toroidal surface i.e. the inside of a tire, and the light receiving apparatus 40 to receive the light from the inside of the outside of a hollow toroidal surface.

Figure 6:
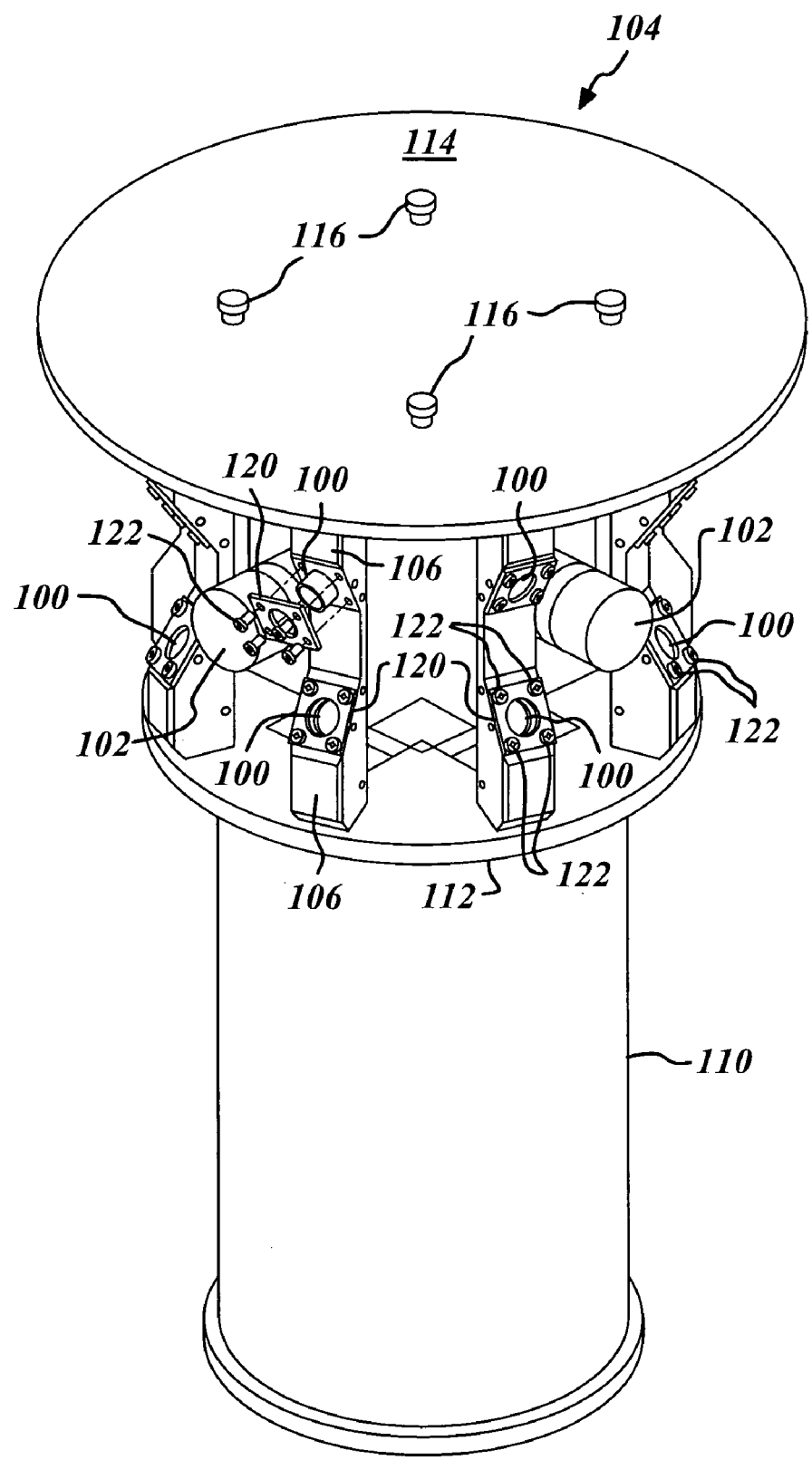
FIG. 6 is a perspective view of a portion of one embodiment of the apparatus of the present invention.
Figure 7:
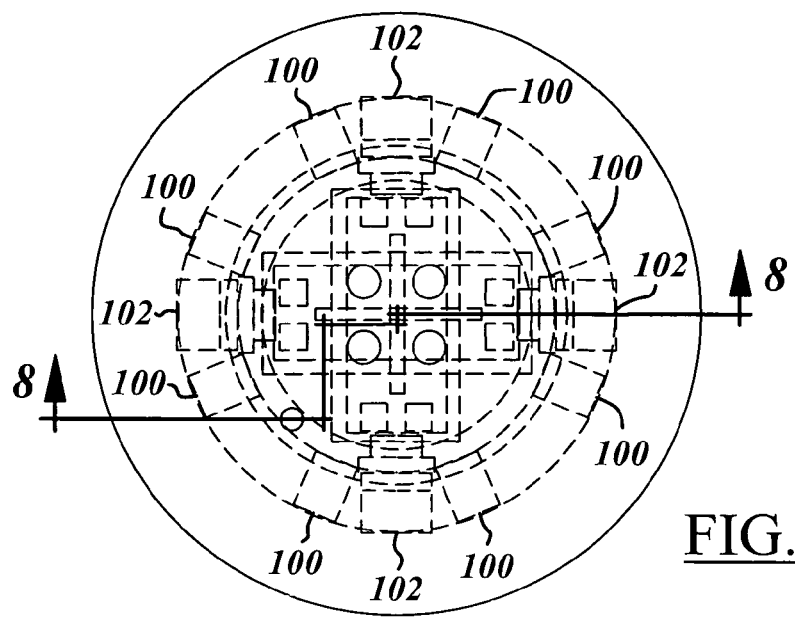
FIG. 7 is top sectional view of the apparatus of FIG. 6.
Figure 8:
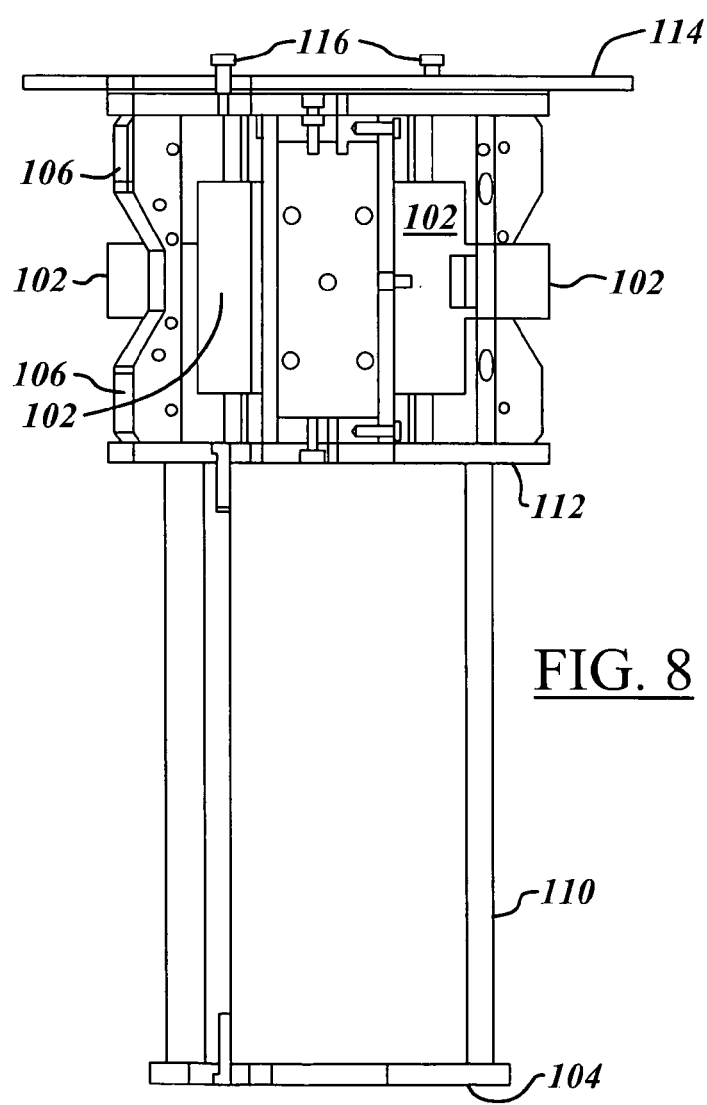
FIG. 8 is a sectional view of FIG. 7 taken along lines 8—8 of FIG. 7.

In FIGS. 6–8A, there are multiple lasers 100, which are located substantially adjacent to the light receiving apparatus 102 preferably a camera. The camera or cameras as shown in FIGS. 6–8 are four in number circumferentially evenly located about a circle sitting atop the mounting plate 112 which moves up and down whenever a horizontally placed tire is inserted into the testing apparatus 10. In one embodiment a CCD camera 102 employed is LUMENERA camera LU105M supplied by Lumenera Corporation because of its thin cross section and the need to have several components back to back in a small space inside the test object (tire).

It is to be appreciated that the number of receiving apparatus 102, and the number of lasers 100 and the number and style of light shaping diffusers can vary depending upon the size of the substrate to be studied, such as 2 to 8 cameras, preferably 4–6. As can be seen from FIG. 6, the lasers point in a direction both upwards, downwards and outwards or could be any combination of angles to suit the shape of the test object through a light shaping elliptical diffuser (not shown) fitting within retaining member 106. As can be seen from FIGS. 6 and 7, the sources of coherent light 100 are placed on each side of the light receiving apparatus 102. Preferably the angle of the source of the lasers to the axis of the light receiving apparatus can vary from 10 to 45 degrees, preferably 20 to 45 degrees (as best seen from top view of FIG. 7).

Figure 8A:
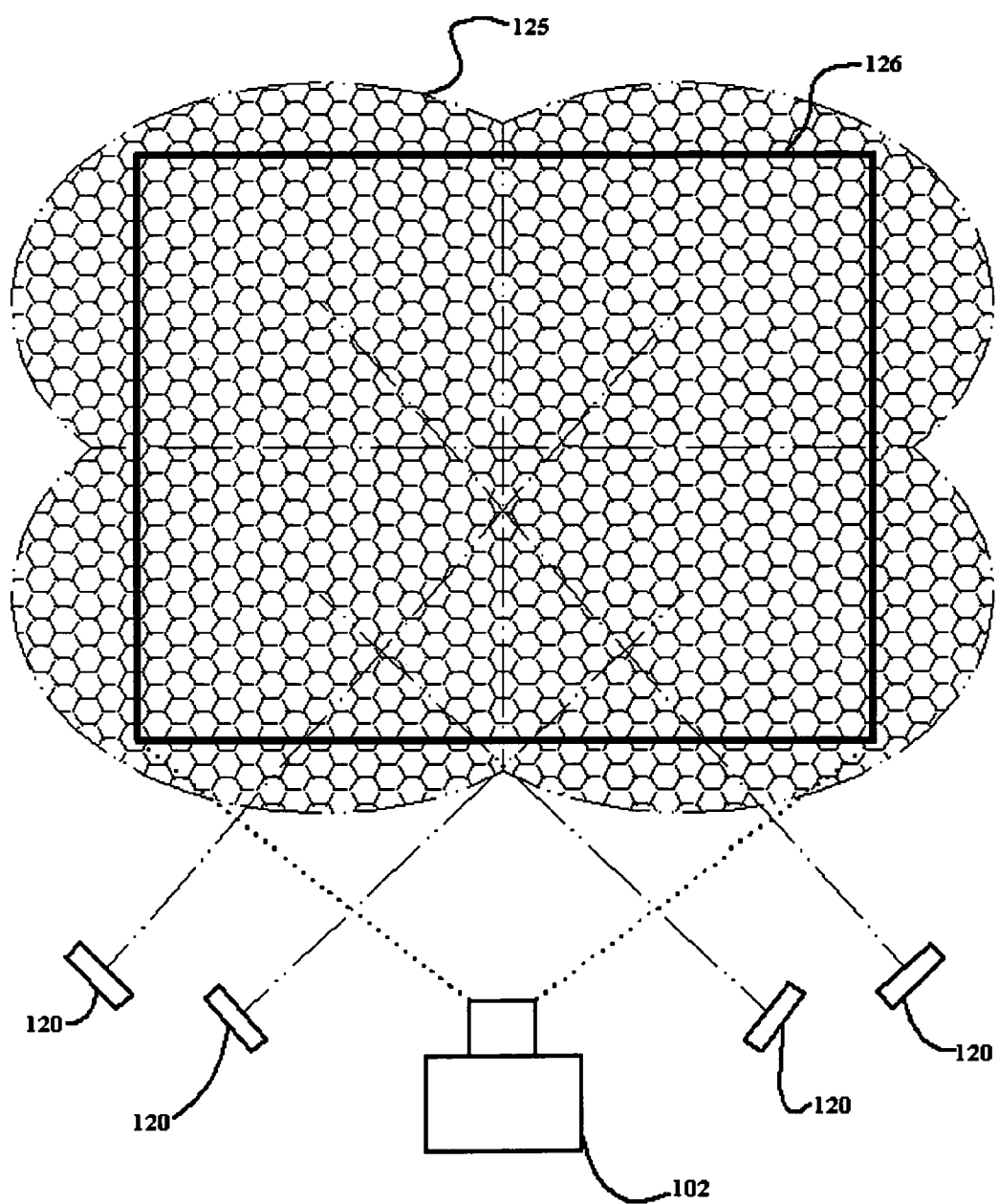
FIG. 8A is a schematic diagram of an imaging arrangement of the apparatus of FIG. 6.
Figure 8B:
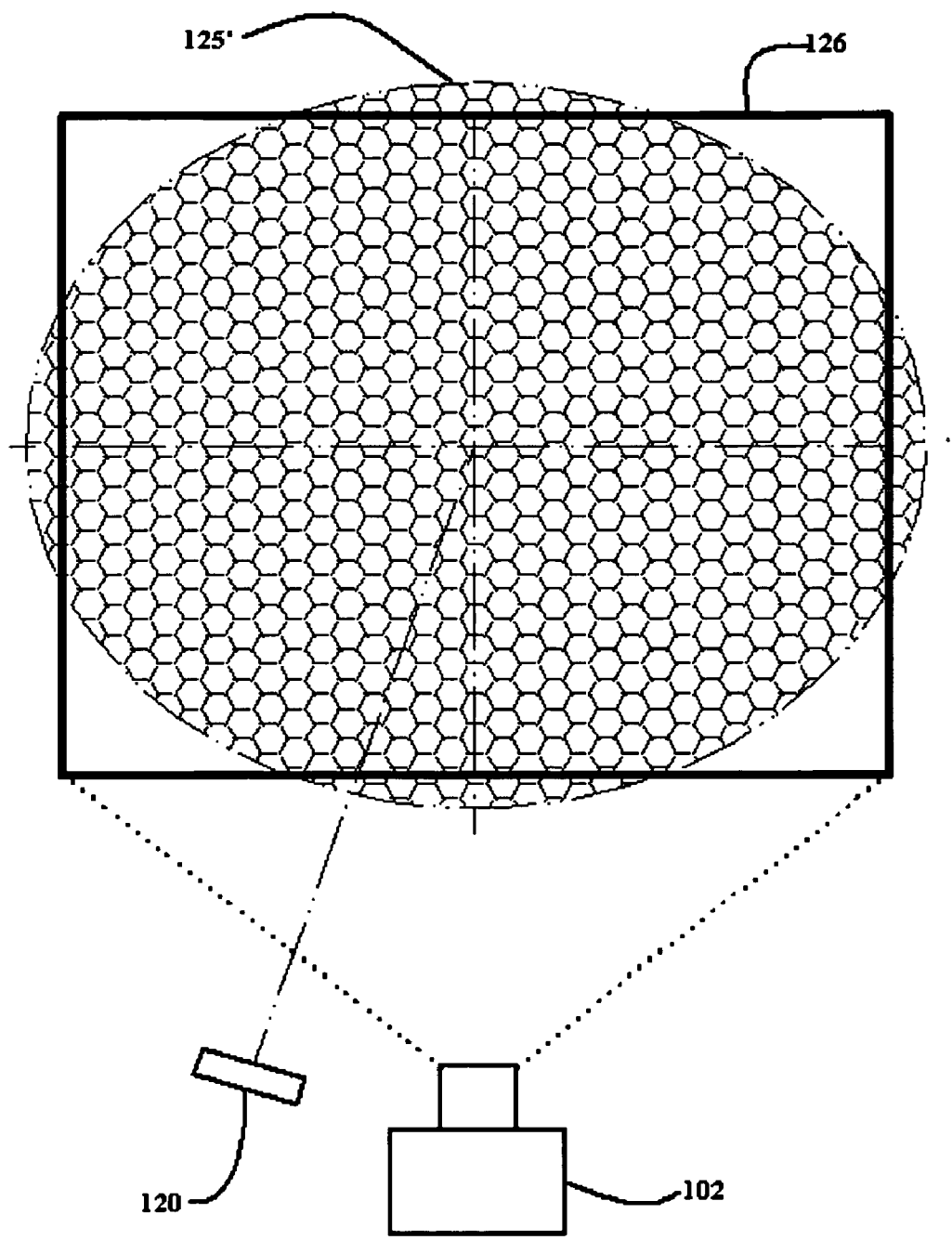
FIG. 8B is a schematic diagram of an alternative imaging arrangement of the apparatus of FIG. 6.

It is likewise to be appreciated that to improve the light distribution to be received by the light receiving apparatus, the number of coherent light sources 100 can be increased from 2 to 8 per light receiving apparatus and that the light source can have an elliptical pattern. For example, FIG. 8A illustrates an imaging arrangement including camera 102 and a plurality of elliptical diffusers 120. Coherent light passes through each diffuser 120 and creates a composite illuminated area 125 composed of smaller overlapping elliptical shaped areas. In turn, the camera 102 captures light reflected from the viewed area 126 of the object that is completely illuminated. FIG. 8B illustrates an alternative imaging arrangement including the camera 102 and the elliptical diffuser 120. Coherent light passes through the diffuser 120 and creates an elliptical shaped illuminated area 125 on an object. In turn the camera 102 "views" or captures light reflected from a viewed area 126.

The elliptical pattern whether it is one or multiples are more conducive to illuminating a rectangular shape which is the output of a camera and the shape of a computer display monitor. The rectangular shape commonly represents an aspect ratio of width to height that in this case is preferably five to four. Additionally another unique feature of this invention is to use the raw rectangular output of the laser to the advantage for an elliptical output. Most laser diodes produce as output a rectangular shaped form of light and then the light is collimated with a lens to form a Gaussian mode ($TEM_{00}$) or round beam. Because a tire quadrant in this case (typical) is 90 degrees, the sectional view is wider than tall, and because a camera has an output that is wider than tall and a computer monitor has a display that is wider than tall and a raw laser output is rectangular, the laser is positioned so that the output is wider than tall utilizing the available light energy efficiently. The collimating lens is removed from the laser and replaced with a elliptical light shaping diffuser from Physical Optics Corporation of Torrance, Calif. For this case the output angle of the diffuser is 95 degrees wide and 35 degrees tall but could be any angle/angles that efficiently illuminates the surface area to be tested. FIGS. 6–8 indicate that there are four light sources per light receiving apparatus 102.

As can be seen from FIG. 6–8, the anomaly detector apparatus or assembly 104 is comprised of a movable support structure 110, which moves up and down, with a pair of plates 112 and 114. Between the plates 112 and 114 are the light generating and the light receiving apparatus, including a plurality of clusters of light sources 100 and light receiving apparatus 102, such as a digital camera. The top plate 114 has four clusters between the top and the bottom plate wherein the clusters are secured in place by bolts 116. The diffuser retainer 120 is held in place by a plurality of screws 122.

Figure 6A:
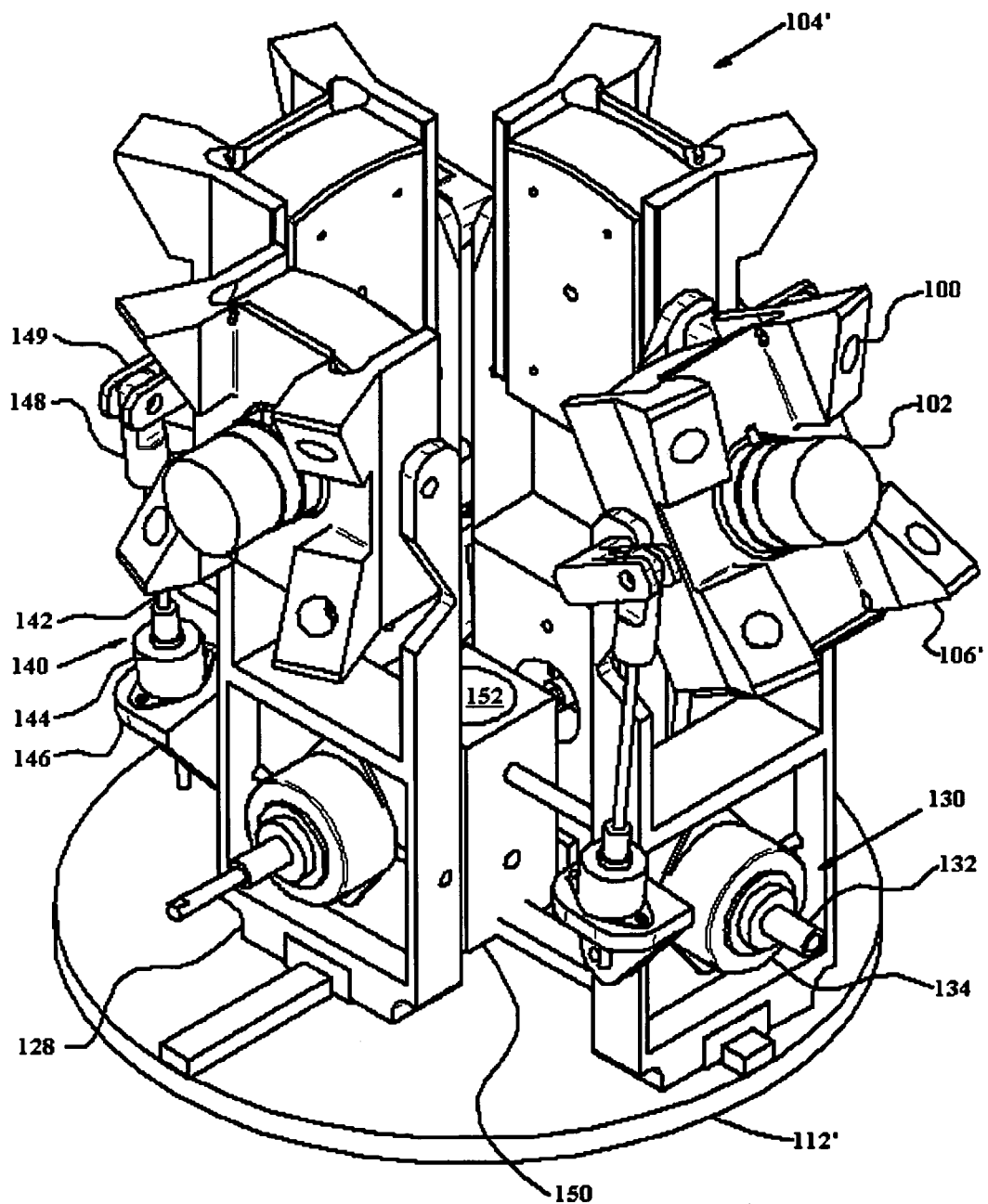
FIG. 6A is a perspective view of a portion of an alternative embodiment of the apparatus of the present invention.

As shown in FIG. 6A, it can also be appreciated that any of the components i.e. light generating and the light receiving apparatus 100, 102, can be moveable in and out or tip as a group or independently for a better view of the substrate to be tested. Alternatively the components 100, 102 may be moved in and out or tip as a group or independently in micro motion to increase the ability of each light sensing sensor in the camera to view one or more reflected laser speckle.

FIG. 6A illustrates an alternative anomaly detector apparatus or assembly 104' including a base plate 112' having a plurality of vertically extending and radially or horizontally translatable uprights 128 mounted thereto via a standard guide or slide arrangement as shown. Any suitable pillow block and guide rail combination, or the like, may be used to mount the uprights 128 to the plate 112'. The uprights 128 are preferably translated using an electromechanical linear actuator 130 including a threaded shaft 132 extending through a threaded motor assembly 134. The motor assembly 130 is preferably a Portescap 40 series linear actuator, available from Danaher Motion of West Chester, Pa. A radially inboard end of the shaft 132 is preferably affixed in any suitable manner to a center support 150, which is fixed to the plate 112' in any suitable manner. The center support 150 includes a passage 152 extending vertically therethrough for communicating power and control wires (not shown) for connection to the motor assembly 134. Portions of the motor assembly 134 rotate to translate the upright 128 back and forth in a horizontal or radial direction. Accordingly, the light sources 100, light receiving apparatuses 102, and diffusers 120 are independently translatable.

Retaining members 106' are pivotably mounted to respective upper ends of the uprights 128 to provide the tipping or tilting functionality referred to above. Accordingly, other electromechanical linear actuators 140, including threaded shafts 142 and motor assemblies 144, are mounted to respective sides of the uprights 128 via mounting brackets 146. The motor assembly 130 is preferably a Portescap 20 series linear actuator, available from Danaher Motion of West Chester, Pa. The threaded shafts 142 are coupled to couplers 148, which are coupled to pivot arms 149 that, in turn, are coupled to the pivotable retaining members 106'. Portions of the motor assembly 144 rotate to thread, or linearly displace, the threaded shafts 142 therethrough to move the pivot arms 146 and thereby pivot, tilt, or tip the retaining members 106'. Accordingly, the light sources 100, light receiving apparatuses 102, and diffusers 120 are independently pivotable.

Figure 9:
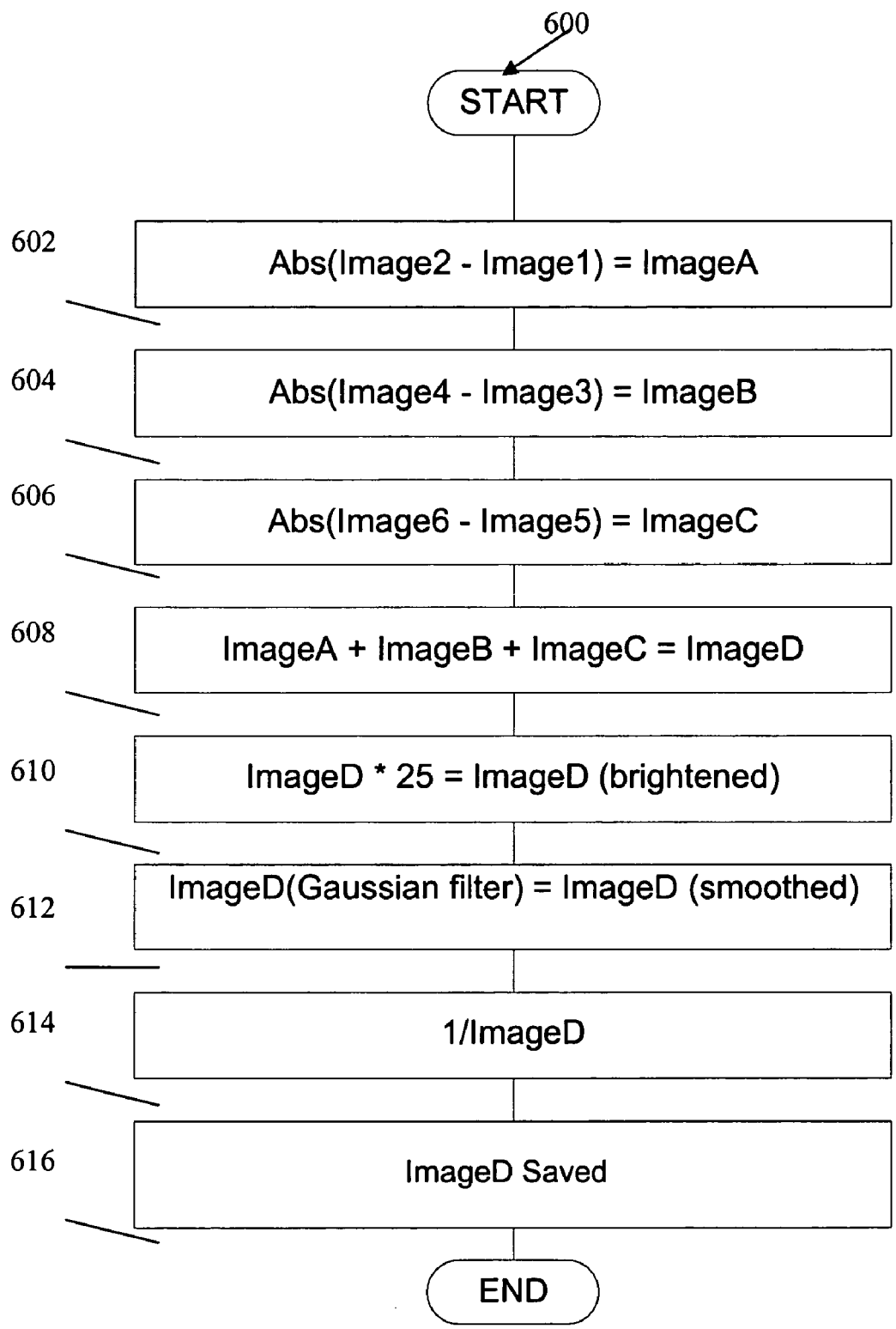
FIG. 9 is a flow chart of an image differencing routine.

To graphically explain how the animation occurs for the apparatus of FIGS. 6–8, reference can be made to FIGS. 4a and 4b and/or FIG. 9. Referring now to the flow chart of FIG. 9, an absolute differencing routine 600 is illustrated and is preferably applied to all of the cameras over a preferred six predetermined test values. After completion of the various computer routines described above, at step 602 the pixel values of a first image, or image 1, of the preferred six images are digitally subtracted (i.e. absolute difference), pixel for corresponding pixel, from the pixel values of a second image, or image 2, of the preferred six images. The resultant differential is stored as image A. If image 1 is a baseline image captured while the object is unstressed or subjected to a "zero" value test level, then image 1 will likely be substantially relatively dark, i.e. registering pixel values closer to 0 than to 255 on the grayscale. If image 2 is an image captured while the object is stressed to some non-zero test level value, then image 2 will exhibit some relatively light areas in the presence of anomalies, registering pixel values progressively away from 0. Again, at step 604, the pixel values of image 3 are digitally subtracted (i.e. absolute difference), pixel for corresponding pixel, from the pixel values of image 4. The resultant differential is stored as image B. Likewise, at step 606, the pixel values of image 5 are digitally subtracted (i.e. absolute difference), pixel for corresponding pixel, from the pixel values of image 6. The resultant differential is stored as image C. Basically, this routine results in differential images A, B, and C that are essentially "spaced" apart from one another along the range of test levels. Steps 602 through 606 are preferably carried out using an Absolute Difference routine of MontiVision.

Software that is utilized to process the speckled image and to display it can be any commercially available image processing software such as PAINT SHOP PRO V. #8.0, supplied by Jasc Software Inc., of Eden Prairie, Minn. Other software that can be used is LabView available from National Instruments of Austin, Tex. or custom written software using an imaging library from the likes of MontiVision of Breiholz, Germany.

FIG. 5 is a representative example of any one of images AA through A_F when the ASTM procedure is utilized except the apparatus of FIGS. 1 and 2 were used in place of an interferometer technique. FIG. 5 shows an image of an ASTM calibration device where the image is a reflected image from the substrate of the calibration device that has been stressed and the laser light has been diffused directly onto the substrate and the reflection of a diffused light is captured as a speckled image by the camera and is stored in the computer memory which in turn can be utilized to generate the output of FIG. 5. It should be noted that the output is characterized as a scaleable representation of the anomaly obtained from the diffused beam of coherent light diffused onto the tire. It should be noted that the image of the reflected light source can be characterized as a scattered speckle reflection. It is to be appreciated that the tire may be in an unstressed and stressed condition or multiple stressed conditions. The computer can compare and display all of the conditions or a portion of them. The invention includes all such comparisons in the completed output form. The output from FIGS. 6–8 can likewise generate the image of FIG. 5.

The utilization of the present technique facilitates quantitative measurement of the anomaly. Alternative to a quantitative determination one can assess the extent of the anomaly by scaling the anomaly with the image that is shown on the computer monitor or is generated in the output such as FIG. 5. Prior art techniques did not permit such measurements or scaling of the anomaly to ascertain the extent of an anomaly in a tire.

The invention described herein in a preferred embodiment does not utilize mirrors for movement of the light. However it is to be appreciated that mirrors may be used to allow the camera to view areas normally inaccessible, depending on the light source, the camera, the diffuser, the test substrate and the number of images to be taken of the substrate. Mirrors may be utilized under particular desired testing techniques and conditions.

The application of the apparatus and method of the present application pertains to a wide variety of substrates that can be stressed, allowing the surface topography to change during stressing. Including but not limited to, any rubber product that has one, or more than one of the following components i.e. reinforcements, backers, strengthening ribs, mounting brackets, cores, honeycombs. These rubber products may be tires (automobile, truck, motorcycle, tractor, construction equipment and aircraft), hoses (radiator, heater, fuel, water, air, hydraulic coil and industrial), belts (fan, power transmission, timing, conveyor such as for mining, and industrial), sheets (pump diaphragms, tank bladders and gaskets) and the like.

A variety of laminated substrates of various plastic materials may be used including thermoplastic, thermoset materials, elastomeric and adhesive materials as well as a wide variety of composites including fiber reinforced composites, metal glass fiber laminates, honeycomb structures, glass or carbon fiber reinforced plastics and the like. The substrates to be tested include a wide variety of vehicle parts such as for cars, trucks, off-road vehicles, aircraft, farming equipment and the like. One can also detect an anomaly in other substrates, such as, honeycomb aluminum panels and other composite panels as well as carbon fiber reinforced plastic specimens. Other multilayer materials or laminates can be reviewed such as metal ceramic, metal plastic and metal glass fiber compound materials such as those used in the electronic industry, aircraft engine parts or parts in the aeronautics industry.

It is to be appreciated that while the drawings show the interior of a tire, (a cross section of the inside of the outside wall of a toroid), a plurality of any of the substrates can be reviewed by having substrate holders for the substrates. Also the wavelength of the light source which is utilized can vary, such as, visible light (about 400–700 nanometers) to near visible or greater than visible light. Also the type of diffuser material including the shape and the angle of the output may also vary. While the invention herein disclosed constitute presently preferred embodiments, many others are possible. It is not intended herein to mention all of the possible equivalent forms or ramifications of the invention. It is understood that the terms used herein are merely descriptive rather than limiting and that various changes may be made without departing from the spirit or the scope of the invention. For example the number and type of lasers to be utilized can vary substantially; the software in the computer that is described herein can be varied depending upon the changes in technology with respect to the computer or computer devices and updates to the types of software.

We claim:

1. An anomaly detector apparatus for detecting an anomaly in a substrate comprising:
   a plurality of sources of coherent light to shine the light directly onto the substrate surface and the light being reflected from the substrate;
   a stressing apparatus, which is juxtaposed to the substrate and which, can optionally, stress the substrate;
   a plurality of reflected light receiving apparatus for receiving the light reflected directly from the substrate whether the substrate is in a stressed or unstressed condition, wherein the sources of light are spaced to shine simultaneously on the entirety of the substrate surface to be tested and all of the receiving apparatus are spaced to receive the reflected light simultaneously to detect an anomaly on all substrate surfaces on which the light is shown;
   a comparator which views and compares images of reflected light from the reflected light receiving apparatus when the substrate is stressed or unstressed thereby ascertaining an anomaly in the substrate and which generates an output from the comparison; and
   a display apparatus electronically connected to the comparator for displaying the output from the comparator.

2. The apparatus of claim 1 wherein there are a plurality of clusters of light sources and light receiving apparatus wherein each cluster has a plurality of light sources that are in a plane and the light sources are spaced near each light receiving apparatus and which plane forms an angle from 10 to 45 degrees with an axis of the light receiving apparatus.

3. The apparatus of claim 1 for detecting an anomaly in a tire.

4. The apparatus of claim 2 wherein there are about 2 to 8 clusters to view the substrate.

5. The apparatus of claim 2 wherein there are 2 to 6 sources of light per light receiving apparatus with one half of the sources spaced 180 degrees from each other spaced about the circumference of the light receiving apparatus.

6. The apparatus of claim 1 where the source of light is a laser.

7. The apparatus of claim 1 further comprising a light shaping elliptical diffuser placed between the source of light and the tire to distribute the light over a portion of the tire surface.

8. The apparatus of claim 3 further comprising a light shaping elliptical diffuser placed between the source of light and the tire to distribute the light over a portion of the tire without breaking the source of light into more than one beam.

9. The apparatus of claim 1 wherein the reflected light receiving apparatus is a camera.

10. The apparatus of claim 5 wherein the camera is electronically connected to a computer.

11. The apparatus of claim 1 wherein the comparator is software operating in a computer which displays the output.

12. A method of detecting an anomaly in a substrate comprising:
providing a plurality of sources of coherent light;
shining the light directly onto the substrate surface, thereby generating a reflected light from the substrate;
stressing the substrate;
providing a plurality of reflected light receiving apparatus for receiving the light reflected directly from the substrate whether the substrate is in a stressed or unstressed condition, wherein the sources of light are spaced to shine substantially simultaneously on the entirety of the substrate surface to be tested and all of the receiving apparatus are spaced to receive the reflected light substantially simultaneously to detect an anomaly on all substrate surfaces on which the light is shown;
providing a comparator which views and compares images of reflected light from the reflected light receiving apparatus when the substrate is stressed or unstressed thereby ascertaining an anomaly in the substrate and generates an output from the comparison; and
displaying, from apparatus electronically connected to the comparator, the output from the comparator.

13. The method of claim 12 wherein there are a plurality of clusters of light sources and light receiving apparatus wherein each cluster has a plurality of light sources that are in a plane and the light sources are spaced near each light receiving apparatus and which plane forms an angle from 10 to 45 degrees with an axis of the light receiving apparatus.

14. The method of claim 12 wherein the substrate to be tested is a tire.

15. The method of claim 13 wherein there are about 2 to 8 clusters to view the interior of a tire.

16. The method of claim 12 wherein there are 2 to 6 sources of light per light receiving apparatus with one half of the sources spaced 180 degrees from each other spaced about the circumference of the light receiving apparatus.

17. The method of claim 11 where the source of light is a laser.

18. The method of claim 12 further comprising distributing the light over a portion of the substrate surface by a light shaping elliptical diffuser placed between the source of light and the tire.

19. The method of claim 13 further comprising distributing the light over a portion of the tire without breaking the source of light into more than one beam by a light shaping elliptical diffuser placed between the source of light and the tire.

20. The method of claim 12 wherein the reflected light receiving apparatus is a camera.

21. The method of claim 12 further comprising passing the images from the camera to a computer.

22. The method of claim 11 wherein the comparator is software operating in a computer which displays the output.

23. The method of claim 13 wherein the output is scaled to size the anomaly in the tire.

24. The method of claim 12 where the output is characterized as a scattered speckle reflection.

25. The method of claim 12 wherein the output is black on white or white on black.

26. The method of claim 12 wherein the output is in multiple colors to enhance visibility of the anomaly.

* * * * *